United States Patent [19]

Stelzer

[11] Patent Number: 5,773,656

[45] Date of Patent: Jun. 30, 1998

[54] PROCESS FOR THE PREPARATION OF OPTICALLY ACTIVE 1-ARYL-ALKYLAMINES

[75] Inventor: Uwe Stelzer, Burscheid, Germany

[73] Assignee: Bayer Aktiengesellschaft, Leverkusen, Germany

[21] Appl. No.: 694,893

[22] Filed: Aug. 9, 1996

[30] Foreign Application Priority Data

Aug. 17, 1995 [DE] Germany .................. 195 30 204.4

[51] Int. Cl.$^6$ .................. C07C 209/00; C07C 69/74; C07C 69/96; A01N 61/00
[52] U.S. Cl. .................. 564/396; 514/1; 514/506; 558/260; 560/1; 560/8; 560/19; 560/20; 564/396
[58] Field of Search .................. 514/1, 506; 558/260; 560/1, 8, 19, 20, 41; 564/396

[56] References Cited

U.S. PATENT DOCUMENTS 4,988,734  1/1991  Kraatz et al. .................. 514/624

FOREIGN PATENT DOCUMENTS 4332738  3/1995  Germany .

OTHER PUBLICATIONS

Solomons "Organic Chemistry" 5th Edition, John Wiley & Sons, Inc., pp. 846–847, 1992.
S. Itsuno, et al., J. Chem. Soc. Perkin. Trans. I., pp. 2030–2044 ) 1985.
S. Itsuno, et al., Chemistry Letters, pp. 1133–1136 (1986).
M.C. de Zoete, et al., J. Chem. Soc., Chem. Commun., pp. 1831–1832 (1993).
C. Bolm, Angew. Chem., vol. 105, No. 2, pp. 245–246 (1993).
Enlish language abstract of JP 5–157,394 (1995).
V. Gotor (Gotor I), "Microbicidal Reagents in Organic Synthesis," pp. 199–208; Kluver Academic Publishers (1992).
V. Gotor, et al. (Gotor II), Tetrahedron vol. 47, No. 44, pp. 9207–9214, (1991).
V. Sanchez, et al., SYNLETT, pp. 529–530 (Jul. 1994).
M. J. Garcia, et al., Tetrahedron, vol. 50, No. 23, pp. 6938–6940 (1994).

*Primary Examiner*—Ardin H. Marschel
*Assistant Examiner*—Jezia Riley
*Attorney, Agent, or Firm*—Sprung Kramer Schaefer & Briscoe

[57] ABSTRACT

Known (R)-1-aryl-alkylamines of the formula

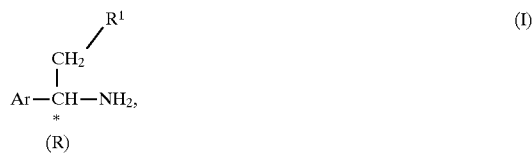

in which $R^1$ and Ar have the meanings indicated in the description, are prepared by a new process, which comprises
a) reacting a racemate of an ethyl or methyl 2-aryl-alkanoate of the formula

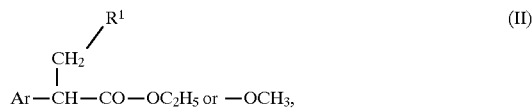

with ammonia in the presence of a lipase which is suitable for the cleavage of esters, in the presence of a diluent,
b) separating off from the reaction mixture the resulting (R)-2-aryl-alkanamide of the formula

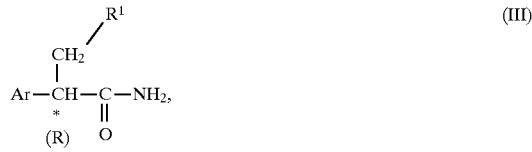

and then reacting it with sodium hypochlorite or sodium hypobromite in the presence of water.

9 Claims, No Drawings

PROCESS FOR THE PREPARATION OF OPTICALLY ACTIVE 1-ARYL-ALKYLAMINES

The present invention relates to a new process for the preparation of (R)-1-aryl-alkylamines, which can be used as intermediates for the synthesis of active compounds having fungicidal properties.

It has already been disclosed that optically active amines can be prepared by reacting racemates of amines with 2-(4-hydroxyphenoxy)-propionic acid, separating off the desired product from the resulting diastereomer mixture and releasing the optically active amine therefrom by treatment with base (cf. JP-A 95-010 813). A disadvantage of this process is that the yields of the desired substances are not always satisfactory and the optical purity of the reaction products especially leaves something to be desired.

Furthermore, it is already known that (R)-1-(4-chloro-phenyl)-ethylamine is obtained when racemic 1-(4-chloro-phenyl)-ethylamine is reacted with (S)-(−)-N-phenylcarbama-lactic acid in the presence of ethanol, and the crystal magma resulting in this process is filtered off with suction and treated with aqueous sodium hydroxide solution in the presence of methylene chloride (cf. EP-A 0 341 475). The economy of this process, however, is adversely affected by the fact that a considerable proportion of (S)-(−)-N-phenylcarbama-lactic acid is present in the mother liquor obtained after suction filtration of the crystal magma and can only be isolated therefrom in a laborious manner.

As is further disclosed in DE-A 4 332 738, optically active primary and secondary amines can be prepared by first acylating racemic amine with certain esters in the presence of a hydrolase, then separating the mixture of optically active amine and optically active acylated amine and thereby obtaining an enantiomer of the amine and optionally obtaining the other enantiomer from the optically active, acylated amine by amide cleavage. When working according to this process, however, in each case only the (S)-amines are formed. In order to obtain the corresponding (R)-amines, a laborious separation of the acylated component and its cleavage are necessary.

It is to be inferred from J. Chem. Soc. Chem. Commun. 1993, 1831–1832 that racemates of 2-chloroethyl 2-(4-isobutyl-phenyl)-propionate can be converted enantioselectively into (R)-2-(4-isobutyl-phenyl)-propionamide with the aid of ammonia in the presence of certain enzymes, such as *Candida antarctica* lipase SP 435. This process, however, is affected by the disadvantage that besides the desired (R)-amide a considerable proportion of free (R)-acid is also formed.

It is moreover known that optically active amines are accessible by enantioselective hydrogenation of C=N bonds in the presence of chiral transition metal complexes (cf. Angew. Chem. 105, 245 (1993)). In addition to a laborious preparation and recycling of the catalysts, this process has the disadvantage that the optical yields are relatively low in some cases.

Finally, it follows from the literature that optically active amines are obtained in good optical yields in the asymmetric reduction of oximes with lithium aluminium hydride, chiral lithium aluminium hydride complexes or chiral borane complexes (cf. Chem. Lett. (1986), 1133 and J. Chem. Perkin Trans. I (1985), 2039). However, for safety reasons this method is only of limited suitability for carrying out on the industrial scale.

It has now been found that (R)-1-aryl-alkylamines of the formula

in which $R^1$ represents hydrogen or alkyl and
Ar represents optionally substituted phenyl of the formula

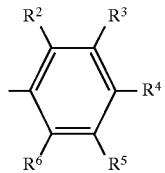

in which
$R^2$ and $R^6$ represent hydrogen or fluorine and
$R^3$, $R^4$ and $R^5$ independently of one another represent hydrogen, halogen, alkyl, halogenoalkyl, alkoxy, halogenoalkoxy, cyano, dialkylamino, nitro, phenyl, phenoxy or benzyl,
or
Ar represents naphthyl which is optionally mono- to trisubstituted by identical or different halogen, alkyl, halogenoalkyl, alkoxy and/or halogenoalkoxy substituents,
are obtained by
a) reacting racemates of ethyl or methyl 2-aryl-alkanoates of the formula

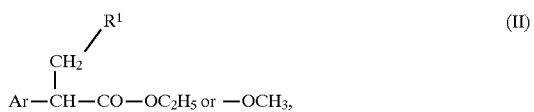

in which
$R^1$ and Ar have the meanings indicated above,
with ammonia in the presence of lipases which are suitable for the cleavage of esters, in the presence of a diluent,
b) separating off from the reaction mixture the resulting (R)-2-aryl-alkanamides of the formula

in which
$R^1$ and Ar have the meanings indicated above,
and then reacting with sodium hypohalites of the formula

NaOHal (IV), in which
Hal represents chlorine or bromine,
in the presence of water.

(R)-1-Aryl-alkylamines are to be understood as meaning those optically active compounds of the formula (I) which have the (R)-configuration on the asymmetrically substituted carbon atom. In the formula (I), the asymmetrically substituted carbon atom is marked by (*). The chiral centres are also marked in the same manner in other formulae.

It is to be noted as extremely surprising that (R)-1-aryl-alkylamines can be prepared by the process according to the invention in high yield and very good optical purity. On the basis of the known prior art, it was for example not to be expected that the less reactive ethyl esters and methyl esters in comparison to the 2-chloroethyl esters would be suitable as starting substances. It is also unexpected that a hydrolysis of the esters employed only takes place to a very small extent.

The process according to the invention has a number of advantages. It thus makes possible the preparation of a multiplicity of (R)-1-aryl-alkylamines in high yield and very good optical purity. It is also convenient that both the starting substances and the reaction components are accessible in a simple manner and are also available in relatively large amounts. It is finally particularly advantageous that the unreacted (S)-2-aryl-alkanoic acid esters in each case can be racemized in a simple manner and used again for resolution.

If racemic ethyl 2-(4-chlorophenyl)-propionate is reacted with lipase from *Candida antarctica* in the presence of ammonia and the amide resulting therefrom is treated, after prior separation, with sodium hypobromite, the course of the process according to the invention can be illustrated by the following reaction scheme.

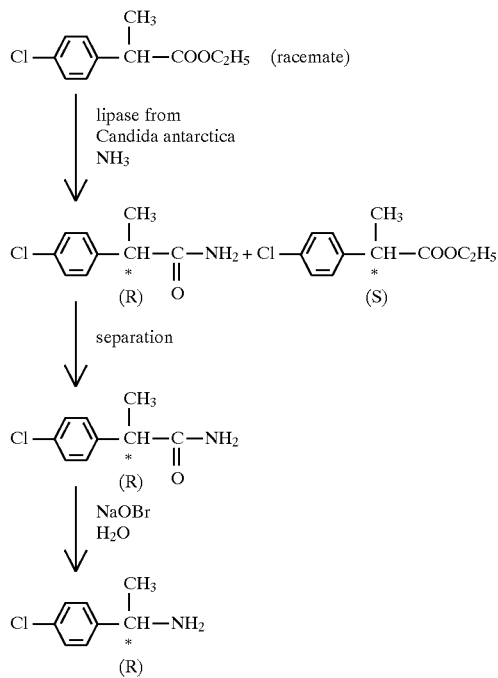

Formula (II) provides a general definition of the racemic ethyl or methyl 2-aryl-alkanoates needed as starting substances when carrying out the process according to the invention. In this formula, $R^1$ preferably represents hydrogen or straight-chain or branched alkyl having 1 to 4 carbon atoms, and Ar represents optionally substituted phenyl of the formula

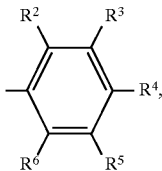

in which
$R^2$ and $R^6$ preferably represent hydrogen or fluorine, at least one of these two substituents representing hydrogen, and
$R^3$, $R^4$ and $R^5$ independently of one another preferably represent hydrogen, fluorine, chlorine, bromine, straight-chain or branched alkyl having 1 to 4 carbon atoms, straight-chain or branched alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, cyano, dialkylamino having 1 to 4 carbon atoms in each alkyl group, nitro, phenyl, phenoxy or benzyl,
or
Ar preferably represents naphthyl which is optionally mono- to tri-substituted by identical or different fluorine, chlorine, bromine, straight-chain or branched alkyl having 1 to 4 carbon atoms, halogenoalkyl having 1 to 4 carbon atoms and 1 to 5 identical or different halogen atoms, alkoxy having 1 to 4 carbon atoms and/or halogenoalkoxy having 1 to 4 carbon atoms and 1 to 5 identical or different halogen atoms, but where the ortho positions to the carbon atom via which the naphthyl radical is bonded are not substituted.

Particularly preferred compounds of the formula (II) are those in which $R^1$ represents hydrogen, methyl, ethyl, n-propyl, isopropyl, n-butyl, iso-butyl or sec-butyl and
Ar represents optionally substituted phenyl of the formula

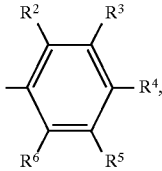

in which
$R^2$ and $R^6$ represent hydrogen or fluorine, at least one of these two substituents representing hydrogen, and
$R^3$, $R^4$ and $R^5$ independently of one another preferably represent hydrogen, fluorine, chlorine, bromine, methyl, ethyl, n-propyl, isopropyl, n-butyl, iso-butyl, sec-butyl, tert-butyl, methoxy, ethoxy, trichloromethyl, trifluoromethyl, difluoromethyl, trifluoromethoxy, difluorochloromethoxy, difluoromethoxy, cyano, dimethylamino, diethylamino, nitro, phenyl, phenoxy or benzyl, or
Ar represents naphthyl which is optionally mono- to trisubstituted by identical or different fluorine, chlorine, bromine, methyl, ethyl, n-propyl, isopropyl, n-butyl, iso-butyl, sec-butyl, tert-butyl, methoxy, ethoxy, trichloromethyl, trifluoromethyl, difluoromethyl, trifluoromethoxy, difluorochloromethoxy and/or difluoromethoxy, but where the ortho positions to the carbon atoms via which the naphthyl radical is bonded are not substituted.

The racemic ethyl or methyl 2-aryl-alkanoates of the formula (II) are known or can be prepared by known methods.

Suitable biocatalysts when carrying out the first stage of the process according to the invention are all those lipases which are selective for the cleavage of the (R)-enantiomers of ethyl 2-aryl-alkanoates of the formula (II) and are suitable for catalyzing amide formation. Examples which may be mentioned are lipase from *Candida antarctica*, Newlase F, lipase from *Pseudomonas sp.* and lipase M. These lipases which can be employed as biocatalysts are known.

The lipases can be employed in carrying out the first stage of the process according to the invention either in native or in modified form, e.g. micro-encapsulated or bonded to inorganic or organic support materials. Possible support materials here are, for example, Celites, zeolites, polysaccharides, polyamides and polystyrene resins.

For aminolysis, ammonia is used when carrying out the first stage of the process according to the invention. This is preferably employed dried, either as a gas or in liquid form.

Suitable diluents when carrying out the first stage of the process according to the invention are preferably tertiary alcohols, such as tert-butanol and 3-methyl-3-pentanol, further ethers, such as dioxane, furan, dimethyl ether, methyl tert-butyl ether and tert-amyl methyl ether, and also acetonitrile and isopropanol. tert-Butanol can particularly preferably be used.

The temperatures when carrying out the first stage of the process according to the invention can be varied within a certain range. In general, the process is carried out at temperatures between −10° C. and 80° C., preferably between 0° C. and 70° C.

When carrying out the first stage of the process according to the invention, the process is carried out either under atmospheric pressure or, if liquid ammonia in a pressure vessel is employed, under the autogenous pressure which is established in this case. However, it is also possible to work at additionally elevated pressure.

When carrying out the first stage of the process according to the invention, in general 0.01 to 0.5 g, preferably 0.01 g to 0.3 g, of lipase is employed relative to 1 g of racemic ethyl or methyl 2-aryl-alkanoate of the formula (II). The amount of ammonia can be varied within a relatively wide range. In general 0.5 mol to 30 mol, preferably 0.5 mol to 10 mol, of ammonia are employed relative to 1 mol of racemic ethyl or methyl 2-aryl-alkanoate of the formula (II). When working with gaseous ammonia, in detail a procedure is used in which the reaction mixture is first treated with ammonia until it is saturated and then ammonia is passed through the reaction vessel until the reaction is complete. When working with liquid ammonia, a procedure is used in which liquid ammonia is condensed at low temperature in a pressure vessel filled with the reaction mixture, then the pressure vessel is closed and warmed to the temperature required in each case. Working up is carried out by customary methods. In general, a procedure is used in which the biocatalyst is separated off, the filtrate is concentrated and the residue which remains is taken up in a suitable solvent mixture so that the desired amide precipitates in solid form and can be filtered off. The ethyl or methyl (S)-2-aryl-alkanoate can be recovered from the filtrate by concentrating under reduced pressure. This can be racemized, for example, by treating with sodium ethoxide in ethanol and used again for resolution.

Suitable hypohalites when carrying out the second stage of the process according to the invention are sodium hypochlorite and sodium hypobromite. In general, a procedure is used in which these substances are freshly prepared by reacting chlorine or bromine with aqueous sodium hydroxide solution and further reaction follows immediately.

The reaction temperatures when carrying out the second stage of the process according to the invention can be varied within a certain range. In general, the process is carried out at temperatures between 0° C. and 120° C., preferably between 20° C. and 100° C.

When carrying out the second stage of the process according to the invention, the process is in general carried out under atmospheric pressure. However, it is also possible to work at elevated pressure.

When carrying out the second stage of the process according to the invention, in general 1.1 to 10 mol, preferably 1.1 to 5 mol, of sodium hypohalite are employed relative to 1 mol of (R)-2-aryl-alkanamide of the formula (III). Working up is carried out by customary methods. In general, a procedure is used in which the reaction mixture is extracted with a poorly water-miscible organic solvent, and the combined organic phases are dried and concentrated under reduced pressure. If appropriate, a further purification of the products obtained can be performed, e.g. by chromatography or distillation.

The (R)-1-aryl-alkylamines of the formula (I) which can be prepared by the process according to the invention are useful intermediates for the preparation of pharmaceuticals or of active compounds having insecticidal, fungicidal or herbicidal properties (cf. EP-A 0 519 211, EP-A 0 453 137, EP-A 0 283 879, EP-A 0 264 217 and EP-A 0 341 475). For example, the fungicidally active compound of the formula

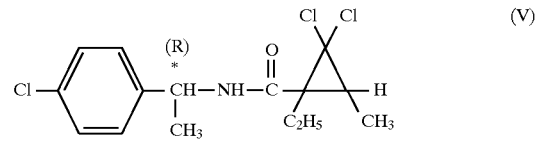

is obtained by reacting (R)-1-(4-chloro-phenyl)-ethylamine of the formula

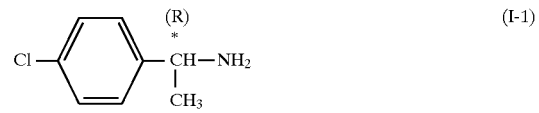

with 2,2-dichloro-1-ethyl-3-methyl-1-cyclopropanecarbonyl chloride of the formula

in the presence of an acid-binding agent and in the presence of an inert organic diluent.

The carrying-out of the process according to the invention is illustrated by the following examples.

PREPARATION EXAMPLES

Example 1

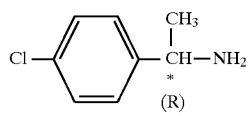

1st stage:

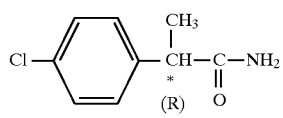

Variant α:

A mixture of 5 g of racemic ethyl 2-(4-chlorophenyl)-propionate and 50 ml of tert-butanol is treated at 50° C. with stirring with 1 g of lipase from *Candida antarctica* (Novozym 435, activity 7000 PLU/g). Ammonia is then passed into the reaction mixture with stirring at 50° C. until it is saturated. The mixture is stirred at 50° C. for a further 28 hours and during the course of this a slow stream of ammonia is continuously passed through the apparatus. The mixture is then worked up by filtering off the biocatalyst, washing it with tert-butanol and ethanol, concentrating the filtrate under reduced pressure and stirring the residue which remains with a mixture of petroleum ether:di-isopropyl ether=9:1. The product obtained in crystalline form is filtered off, washed with petroleum ether and dried. In this manner 1.78 g (42.8% of theory, conversion 44 area per cent GC) of (R)-2-(4-chloro-phenyl)-propionamide having an ee value of 96.1% are obtained.

Variant β:

A mixture of 5 g of racemic ethyl 2-(4-chloro-phenyl)-propionate and 50 ml of tert-butanol is added to an autoclave at room temperature and treated with 1 g of lipase from *Candida antarctica* (Novozym 435, activity 7000 PLU/g). The mixture is then cooled to −50° C. and 0.5 g of ammonia is condensed into the reaction mixture. The pressure vessel is sealed, warmed to 50° C. and the mixture is allowed to react for 24 hours with stirring. It is then worked up in the manner described above. 1.78 g (42.8% of theory) of (R)-2-(4-chloro-phenyl)-propionamide having an ee value of 99.1% are obtained.

2nd Stage

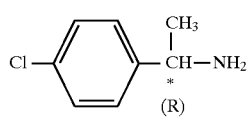

(I-1)

4.4 g (0.0275 mol) of bromine are added dropwise at 0° C. with stirring to a solution of 5.5 g (0.137 mol) of sodium hydroxide in 45 ml of water. The resulting mixture is cooled to −5° C. and treated with stirring with 4.2 g (0.0229 mol) of (R)-2-(4-chloro-phenyl)-propionamide (ee value 98%). The mixture is then heated to 50° C. for 5 hours. After cooling to room temperature, the reaction mixture is extracted three times with methylene chloride, and the combined organic phases are dried over sodium sulphate and concentrated under reduced pressure. In this manner, a product is obtained which, according to the gas chromatogram, consists to 87% of (R)-1-(4-chloro-phenyl)-ethylamine (ee value >98%). Accordingly, a yield of 78.5% of theory is calculated.

Example 2

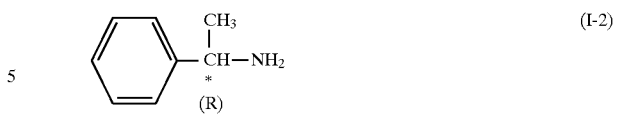

1st stage:

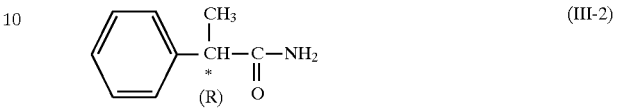

A mixture of 1.6 g of ethyl 2-phenyl-propionate and 18 ml of tert-butanol is treated at 50° C. with stirring with 0.35 g of lipase from *Candida antarctica* (Novozym 435, activity 7000 PLU/g). Ammonia is then passed into the reaction mixture with stirring at 50° to 53° C. until it is saturated. The mixture is stirred at 50° to 53° C. for a further 8 hours and during the course of this a slow stream of ammonia is continuously passed through the apparatus. The mixture is then worked up in the manner indicated in Example 1. 0.6 g (90% of theory, conversion 46 area per cent GC) of (R)-2-phenyl-propionamide having an ee value of >98% is obtained.

2nd stage:

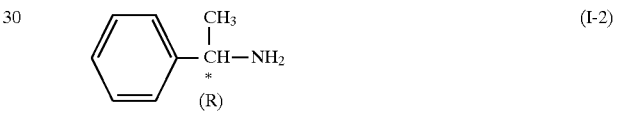

A mixture of 6 g (0.04 mol) of (R)-2-phenyl-propionamide, 4 g (0.1 mol) of sodium hydroxide and 30 ml of water is treated at room temperature with stirring with 48 g (0.084 mol) of sodium hypochlorite solution (content of active chlorine: 12.5%). The mixture is then heated at 80° C. for 4 hours. After cooling to room temperature, the reaction mixture is extracted three times with 75 ml of methylene chloride each time, and the combined organic phases are dried over sodium sulphate and concentrated under reduced pressure. In this manner, 4.7 g of a product are obtained which, according to the gas chromatogram, consists to 85% of (R)-1-phenyl-ethylamine (ee value >98%). Accordingly, a yield of 82.5% of theory is calculated.

It is understood that the specification and examples are illustrative but not limitative of the present invention and that other embodiments within the spirit and scope of the invention will suggest themselves to those skilled in the art.

What is claimed is:

1. A process for the preparation of an (R)-1-aryl-alkylamine of the formula

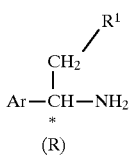

in which $R^1$ represents hydrogen or straight-chain or branched alkyl having 1 to 4 carbon atoms, and Ar represents a phenyl radical of the formula

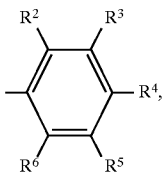

in which
R² and R⁶ represent hydrogen or fluorine, at least one of these two substituents representing hydrogen, and
R³, R⁴ and R⁵ independently of one another represent hydrogen, fluorine, chlorine, bromine, straight-chain or branched alkyl having 1 to 4 carbon atoms, straight-chain or branched alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, cyano, dialkylamino having 1 to 4 carbon atoms in each alkyl group, nitro, phenyl, phenoxy or benzyl,
or
Ar represents naphthyl or represents mono- to trisubstituted naphthyl, the substituents being identical or different and being selected from the group consisting of fluorine, chlorine, bromine, straight-chain or branched alkyl having 1 to 4 carbon atoms, halogenoalkyl having 1 to 4 carbon atoms and 1 to 5 identical or different halogen atoms, alkoxy having 1 to 4 carbon atoms and/or halogenoalkoxy having 1 to 4 carbon atoms and 1 to 5 identical or different halogen atoms, but where the ortho positions to the carbon atom via which the naphthyl radical is bonded are not substituted,
which process comprises
a) reacting a racemate of an ethyl or methyl 2-aryl-alkanoate of the formula

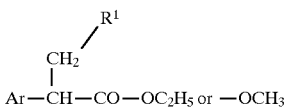

in which
R¹ and Ar have the meanings indicated above,
with ammonia in the presence of a lipase which is suitable for the cleavage of esters, in the presence of a diluent,
b) separating off from the reaction mixture the resulting (R)-2-aryl-alkanamide of the formula

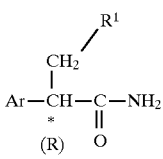

in which
R¹ and Ar have the meanings indicated above,
and then reacting it with a sodium hypohalite of the formula NaOHal in which Hal represents chlorine or bromine,
in the presence of water.
2. A process according to claim 1, wherein the starting substance is a racemate of an ethyl or methyl 2-aryl-alkanoate, in which
R¹ represents hydrogen, methyl, ethyl, n-propyl, isopropyl, n-butyl, iso-butyl or sec-butyl and
Ar represents a phenyl radical of the formula

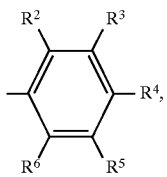

in which
R² and R⁶ represent hydrogen or fluorine, at least one of these two substituents representing hydrogen, and
R³, R⁴ and R⁵ independently of one another represent hydrogen, fluorine, chlorine, bromine, methyl, ethyl, n-propyl, isopropyl, n-butyl, iso-butyl, sec-butyl, tert-butyl, methoxy, ethoxy, trichloromethyl, trifluoromethyl, difluoromethyl, trifluoromethoxy, difluorochloromethoxy, difluoromethoxy, cyano, dimethylamino, diethylamino, nitro, phenyl, phenoxy or benzyl, or
Ar represents naphthyl or mono- to trisubstituted naphthyl, the substituents being identical or different and being selected from the group consisting of fluorine, chlorine, bromine, methyl, ethyl, n-propyl, isopropyl, n-butyl, iso-butyl, sec-butyl, tert-butyl, methoxy, ethoxy, trichloromethyl, trifluoromethyl, difluoromethyl, trifluoromethoxy, difluorochloromethoxy and/or difluoromethoxy, but where the ortho positions to the carbon atoms via which the naphthyl radical is bonded are not substituted.
3. A process according to claim 1, wherein racemic ethyl 2-(4-chlorophenyl)-propionate of the formula

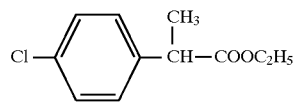

is employed as starting substance.
4. A process according to claim 1, wherein racemic ethyl 2-phenyl-propionate of the formula

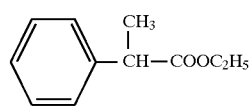

is employed as starting substance.
5. A process according to claim 1, wherein lipase from *Candida antarctica* is employed as biocatalyst.
6. A process according to claim 1, wherein a tertiary alcohol, an ether, acetonitrile or isopropanol is employed as a diluent in carrying out the first stage.
7. A process according to claim 1, wherein the first stage is carried out at a temperature between −10° C. and +80° C.
8. A process according to claim 1, wherein the second stage is carried out at a temperature between 0° C. and +120° C.

9. A process according to claim 1, in which the ethyl or methyl 2-arylalkanoate is selected from the group consisting of racemic

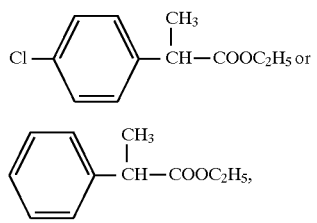

the lipase is from *Candida antarctica*, a tertiary alcohol, an ether, acetonitrile or isopropanol is employed as a diluent in carrying out the first stage which is carried out at a temperature of between −10° C. and +80° C., and the second stage is carried out at a temperature of between 0° C. and +120° C.

* * * * *